United States Patent [19]

Hannula et al.

[11] Patent Number: 4,634,427

[45] Date of Patent: Jan. 6, 1987

[54] IMPLANTABLE DEMAND MEDICATION DELIVERY ASSEMBLY

[75] Inventors: Donald L. Hannula, San Luis Obispo; Frederick L. Coe, Santa Barbara, both of Calif.

[73] Assignee: American Hospital Supply Company, Deerfield, Ill.

[21] Appl. No.: 646,998

[22] Filed: Sep. 4, 1984

[51] Int. Cl.$^4$ ............................................. A61M 5/00
[52] U.S. Cl. ...................................... 604/93; 604/185
[58] Field of Search ................. 604/93, 185, 181, 891

[56] References Cited

U.S. PATENT DOCUMENTS

| | | | |
|---|---|---|---|
| 3,769,982 | 11/1973 | Schulte | 604/10 |
| 3,827,439 | 8/1974 | Schulte et al. | 604/185 X |
| 4,013,074 | 3/1977 | Siposs | 604/891 |
| 4,190,040 | 2/1980 | Schulte | 128/1 R |
| 4,258,711 | 3/1981 | Tucker et al. | 604/93 X |
| 4,437,457 | 3/1984 | Trick et al. | 128/DIG. 25 X |
| 4,544,371 | 10/1985 | Dormandy, Jr. et al. | 604/185 X |

FOREIGN PATENT DOCUMENTS 0143503  6/1985  European Pat. Off. .
8001755  9/1980  World Int. Prop. O. .

OTHER PUBLICATIONS

Medical Progress Through Technology, vol. 9, No. 1, 1982, pp. 17-25, Berlin; G. A. Carlson et al., "An Implantable Remotely Programmable Insulin Infusion System", (p. 1, cols. 1, 2; FIG. 4).

*Implantable Drug-Delivery Systems*, by Perry Blackshear, Scientific American, Dec. 1979, pp. 66-73.

*Insulin Infusion Pumps in the Treatment of Diabetes*", by Perry Blackshear, Medical Instrumentation, vol. 16, No. 1, Jan.-Feb. 1982.

Primary Examiner—William H. Grieb
Attorney, Agent, or Firm—Roger A. Williams; Richard L. Myers; Robert E. Hartenberger

[57] ABSTRACT

An implantable demand medication delivery assembly for delivering measured aliquots of liquid medication. The assembly includes a reservoir which stores the liquid medication to be delivered. The assembly also includes a pump which is in fluid communication with the reservoir. The pump includes a housing having an inlet port in fluid communication with the reservoir and an outlet port. Connected to the outlet port is a delivery catheter for delivering the liquid medication to a site within the patient wherein the assembly is implanted. The pump also includes a fluid passage which extends between the inlet and outlet port. A chamber is provided along the fluid passage for containing a preselected volume of liquid medication to be delivered. A resilient deformable wall on the pump extends over the chamber. A one-way valve is provided in the fluid passage between the inlet port and chamber for permitting fluid flow toward the chamber. A pressure regulated valve is provided in the fluid passage between the chamber and outlet port for selectively permitting fluid flow through the delivery catheter upon actuation of the pump. A puncturable and resealable injection site can also be part of the assembly and, when part of the assembly, is in fluid communication with the reservoir.

21 Claims, 3 Drawing Figures

IMPLANTABLE DEMAND MEDICATION DELIVERY ASSEMBLY

BACKGROUND OF THE INVENTION

The invention herein is directed to an implantable demand medication delivery assembly. In particular, the assembly is designed to be implanted in a patient who requires repeated injections of a particular medication or who requires delivery of a chemotherapeutic agent to a particular location within the patient. The assembly herein can be implanted in a patient and thereby maintain the patient in an ambulatory state without the need for the patient to return to a clinic or hospital environment for treatments and the administration of medication.

There are many patients that have the need for the delivery of a specific dose of medication at various times. For example, many cancer patients, such as those having terminal lower torso cancer, can have symptoms of chronic pain sufficient to render the patient immobile. One routine regimen for treating such patients is the routine injection of morphine into the lumbar region of the patient either epidurally or intrathecally. Such morphine injections have been shown to relieve the symptoms of pain, and in many instances, without adversely affecting the patient's mobility or other routine and normal functions.

Another chronic ailment which requires routine injections is diabetes. Diabetics require frequent dosages of insulin in the treatment of the chronic condition.

It would be desirable to provide an implantable assembly which can deliver a periodic bolus of medication to a specific anatomical area as required by the patient. It would be desirable to have such an assembly that can be operated by the patient. Such an assembly could be used to deliver morphine to the epidural or intrathecal space for pain relief, to deliver chemotherapeutic agents into a feeding artery for cancer treatment, to deliver insulin for diabetics, and to deliver hormone agents for the treatment of sterility and the like.

SUMMARY OF THE INVENTION

The invention herein is directed to an implantable demand medication delivery assembly. In particular, the assembly can be implanted in a patient's body and provide a reservoir of a liquid medication which can be incrementally delivered to a specific site within the patient's body upon demand by actuation of the patient through application of an external force; i.e., finger pressure.

The implantable demand medication delivery assembly herein includes a reservoir constructed of a biocompatible material which can be implanted in the patient's body. The assembly also includes an implantable pump which is connected in fluid communication with the reservoir. The pump includes a reservoir chamber of a preselected volume which corresponds with the volume for a prescribed dosage of medication to be delivered. The reservoir chamber in the pump has a volume which will deliver the prescribed dosage.

The pump also includes a pressure regulated valve between the reservoir chamber and an outlet port on the pump. The pressure regulated valve maintains the liquid medication in the reservoir chamber and prevents its outflow until the pump is intentionally actuated by application of an external force, such as finger pressure. At the time the pump is actuated, the pressure in the reservoir chamber is sufficient to open the pressure regulated valve and permit the medication to flow through the outlet port.

The assembly also includes a one-way valve provided in the fluid passage between the reservoir and the reservoir chamber in the pump. Such a one-way valve permits the flow of liquid medication into the reservoir chamber in the pump and prevents the flow of liquid medication from the reservoir chamber in the pump toward the reservoir itself. The presence of the one-way valve prevents the misdirection of the bolus of medication stored in the reservoir chamber in the pump. That is, the presence of the one-way valve insures that the dosage of liquid medication will be delivered through the outlet port of the pump rather than through the inlet port. Such a one-way valve can be a valve, such as a flap valve, present in the reservoir chamber of the pump and which occludes the fluid passage providing communication between the reservoir and the reservoir chamber in the pump. A flap valve can occlude the fluid passage when the proper volume of liquid medication is present in the reservoir chamber of the pump. The one-way valve can also be a miter valve present in the fluid passage between the reservoir and the reservoir chamber of the pump.

The pump includes a base and an upper wall. The upper wall includes a portion forming a dome, which dome portion is resilient and deformable. The dome portion of the upper wall extends over and defines the reservoir chamber in the pump. Upon deformation of the dome portion of the upper wall, the dosage of liquid medication present in the reservoir chamber can be administered.

Extending around the dome portion of the upper wall can be a toroidal protrusion or extension of the upper wall. Such a toroidal shape of the upper wall encircles and surrounds the dome portion. The toroidal portion of the upper wall also extends to a height which is greater than the height of the dome portion of the upper wall. The greater height of the toroidal portion protects the dome portion from inadvertent deformation and thereby also inadvertent delivery of a dosage of medication. The toroidal portion of the upper wall permits palpation of the pump when the pump is implanted in a position where it can be palpated. A patient can thereby readily locate the pump and thereby also the dome portion upon which a force can be applied for actuating the pump and delivering the medication.

Connected to the outlet port of the pump is a delivery catheter. The delivery catheter is a tubular conduit having a provided opening at its end or having an exit port through which the medication can be delivered to the appropriate site in the patient's body. For example, the catheter can be provided with either an opening or a slit which opens upon a preselected fluid pressure being achieved in the lumen of the delivery catheter.

The assembly can also include an injection site which can be implanted in the patient's body. Such an injection site is implanted such that it is in fluid communication with the reservoir. The presence of an injection site can provide for the replenishing of liquid medication in the reservoir. An injection site is a puncturable and resealable housing which can be punctured with a needle cannula of a syringe for introducing additional medication to the overall assembly and primarily the reservoir. The liquid medication introduced through the injection site flows to the reservoir due to the presence of the one-way valve in the pump of the assembly.

BRIEF DESCRIPTION OF THE DRAWINGS

The implantable demand medication delivery assembly herein can be understood with regard to the following detailed description, accompanying claims and the accompanying drawings wherein:

DETAILED DESCRIPTION

Figure 3:
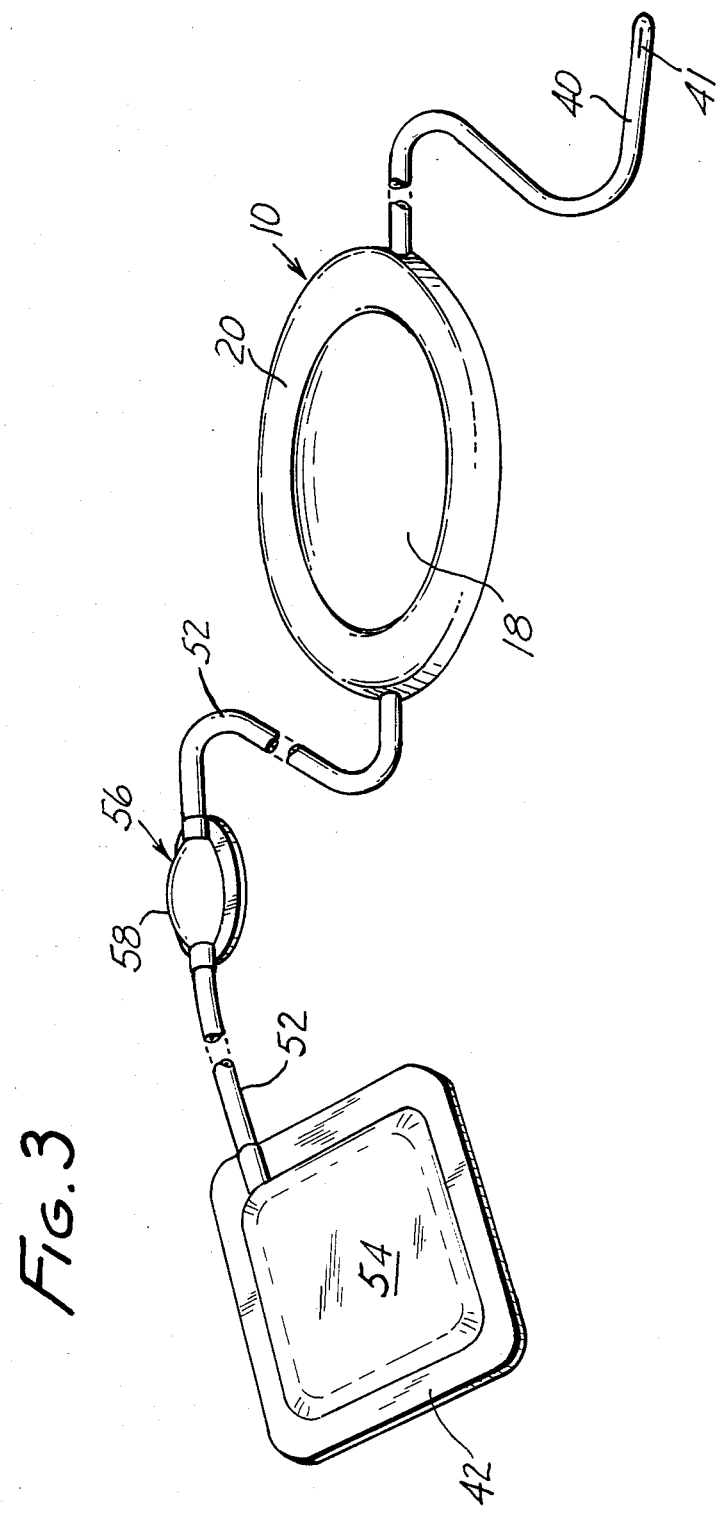
FIG. 3 is a perspective view of the implantable demand medication delivery assembly herein.

The implantable demand medication delivery assembly herein will be described with regard to the accompanying drawings. In particular, FIG. 3 shows a perspective view of the implantable demand medication delivery assembly. The implantable demand medication delivery assembly includes a reservoir 42, an injection site 56, a pump 10, and a delivery catheter 40. In FIG. 3, the relative sizes of the reservoir, injection site and pump are shown in one specific proportion, but for purposes of the implantable demand medication delivery assembly herein, the components can be of any particular size and volumes. For example, the reservoir is an expandable reservoir and is usually designed to retain a sufficient volume of liquid medication for delivering incremental dosages thereof over an extended period of time.

In regard to FIG. 3, the overall assembly herein includes a reservoir 42 for holding a predetermined volume of the liquid medication to be administered. The reservoir 42 includes an expandable wall 54 which can expand with inflation of the reservoir 42 due to the introduction of the liquid medication to the reservoir.

The reservoir 42 is in fluid communication through a tubular conduit 52 with an inlet on a puncturable and resealable injection site 56. Such an injection site can include a puncturable and resealable dome 58. The injection site includes an outlet which is in fluid communication through a tubular conduit 52 with pump 10. With regard to FIG. 3, the pump 10 includes an upper wall having an outer toroidal portion 20 encircling and extending above an inner dome portion 18. Extending from the pump is a delivery catheter 40 having a provided opening, such as a slit 41 at its tip.

The assembly is constructed of a biocompatible material such that it can be readily implanted in a patient's body. A particularly preferred material for constructing the overall assembly is silicone elastomer as silicone elastomer has been proven to be substantially biocompatible with various environments in the body.

Figure 1:
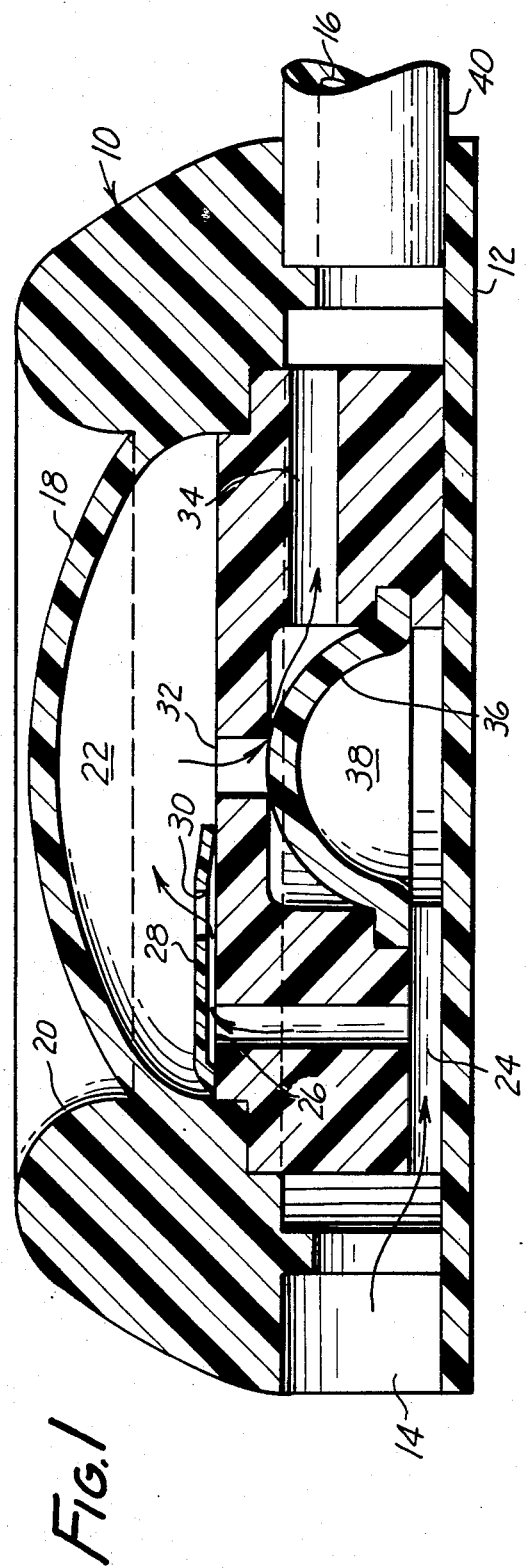
FIG. 1 is a side elevational view in cross section of a pump for use in the implantable demand medication delivery assembly herein.
Figure 2:
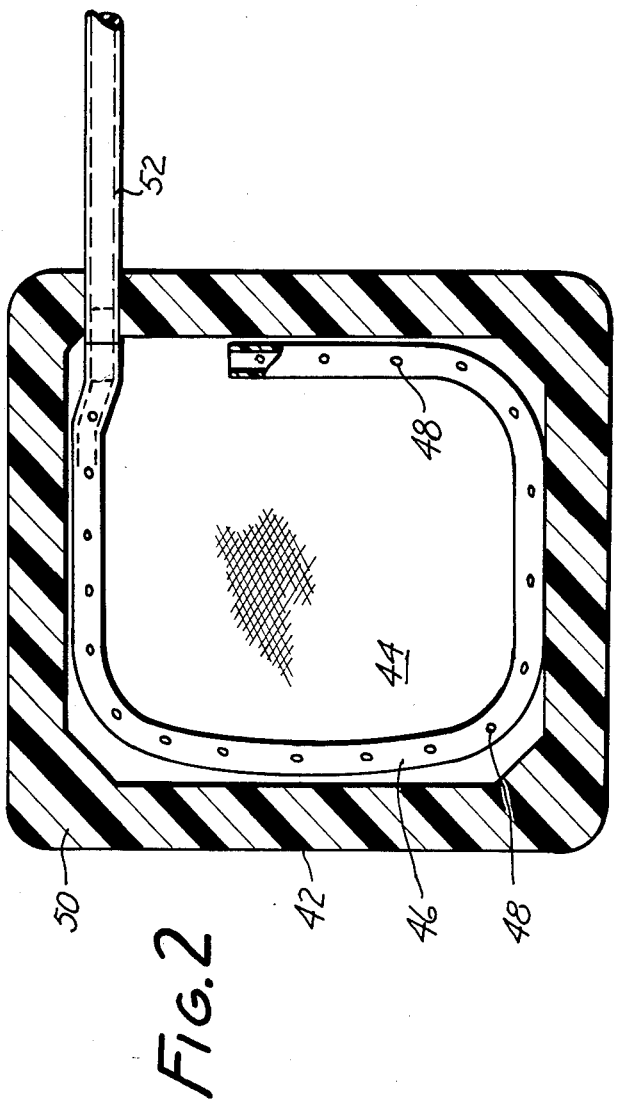
FIG. 2 is a top view in cross section of an implantable reservoir for use in the implantable demand medication delivery assembly herein.

The pump 10 is the primary driving force in the assembly as it receives the liquid medication, provides the proper volume of the liquid medication and delivers the prescribed volume of medication as demanded. The pump 10 is illustrated in FIG. 1. FIG. 1 shows an enlarged elevational view in section of the pump 10. With regard to FIG. 1, the pump consists of a housing defined by a base 12 and a sidewall which, for simplicity and ease of understanding, will be referred to as an upper wall attached to the base. The upper wall includes a first dome-shaped portion 18 and a second toroidal-shaped portion 20 encircling and extending above the dome-shaped portion 18. That is, the toroidal portion 20 extends to a greater height or elevation than the dome portion 18. The upper wall is constructed of a resilient material, such as silicone; the upper wall being constructed of a resilient and elastomeric material in order to make the upper wall deformable and, in particular, the dome portion 18 readily deformable. In order to prevent the inadvertent deformation of the dome portion 18, the toroidal portion 20 encircles and extends to a greater height than the dome portion as shown in FIG. 1. Thus, any inadvertent bumping of the overall pump housing does not deform the dome portion 18 and thereby deliver an unnecessary dose of medication. The toroidal portion thereby provides an important safety feature in the pump assembly.

The pump includes an inlet port 14 providing a site for connection to the appropriate tubular conduit for fluid communication between the pump and reservoir. The pump also includes an outlet port 16 which, through appropriate tubular connections, provides fluid flow passage to the delivery catheter 40.

The pump includes a first fluid passage 24 which extends from the inlet port 14 to a reservoir chamber 22 within the pump. As shown in FIG. 1, the first fluid passage extends through a portion of the base of the pump. The reservoir chamber 22 is defined by the dome portion 18 of the upper wall and base member of the pump. The first fluid passage 24 opens into the reservoir chamber 22 at a first port 26 provided on the base portion of the pump. The reservoir chamber 22 can be of any preselected size which provides the desired volume of liquid medication to be administered upon actuation of the pump. The reservoir chamber 22 is constructed of a size and volume which approximates the volume of the prescribed dosage of medication to be delivered at any given time to the patient in which the overall assembly is implanted. Preferably, the reservoir chamber is of a sufficiently small volume that more than one activation of the pump is required to deliver the prescribed unit dose of medication. Thus, if one dosage is administered inadvertently, it generally will not be of such a sufficient volume as to cause a problem, such as overdosing.

Provided along the first fluid passage either in the pump or along the tubing 52 is a one-way valve, such as a flap valve. The flap valve can be attached to the base of the pump and can lie within the reservoir chamber. The flap valve can be attached along one edge such that it can open or close the first port 26 to fluid flow depending on whether a higher pressure is realized in the first flow passage 24 or in the reservoir chamber 22.

The one-way valve can also be a dome valve 28 which is attached along its periphery to the base. Such a dome valve 28 is illustrated in FIG. 1. The dome valve 28 includes an opening 30 which is not aligned with the first port 26. The term "dome" is used merely to refer to the flap valve being attached at its periphery and which allows flow beteen the flap and base and out through the opening. When the fluid pressure in the first flow passage 24 is greater than that in the reservoir chamber 22, fluid flows out of the first port between the valve 28 and base and into the chamber through the opening 30 in the valve. If the fluid pressure in the reservoir chamber 22 is greater than the fluid pressure in the first fluid flow passage 24, then the fluid in the reservoir chamber exerts a force on the valve, occluding the passage between the valve and base, thereby preventing fluid flow out of or into the chamber. That is, the first port is effectively closed due to the presence of the desired volume of liquid medication in the reservoir chamber. The flap valve thus functions as an anti-backflow valve preventing flow from the chamber through the first port.

The pump also includes a second fluid flow passage 34 which extends between the reservoir chamber 22 and an outlet port 16 on the pump. The second fluid flow passage opens into the reservoir chamber through a second port 32 in the base. A pressure regulated valve is positioned in the second fluid flow passage 34. Such a valve can be any valve which opens at a preselected pressure being realized in the reservoir chamber 22. As the valve opens, the liquid medication in the reservoir chamber can flow out of the reservoir chamber, through the second fluid flow passage, and outwardly through the outlet port 16 on the pump. A preferred pressure regulated valve is a dome-shaped valve 36 which is provided in a valve chamber 38 along the second fluid flow passage 34 and which is open to the first fluid flow passage below the dome-shaped valve.

As shown in FIG. 1, the dome-shaped valve 36 in the valve chamber 38 provides a pressure regulated valve. The dome-shaped valve is balanced against three pressures, namely the fluid pressure in the first fluid flow passage; the fluid pressure in the chamber; and the fluid pressure in the second fluid flow passage. The first fluid flow passage is open to below the dome-shaped valve 36 and thereby exhibits a fluid pressure which urges the dome-shaped valve against the second port 32, thereby occluding the port to fluid flow. Normally, the pressure in the first fluid flow passage is sufficient to maintain the dome-shaped valve in a closed position, closing the second port 32 to fluid flow. As a pressure is exerted on the dome portion of the upper wall, a greater pressure is translated to the fluid within the chamber. At the time the fluid pressure in the chamber overcomes the pressure in the first fluid flow passage, the dome-shaped valve opens, thereby permitting fluid flow from the reservoir chamber 22, through the second port 32, and through the outlet port 16.

Connected to the outlet port 16 of the pump is a delivery catheter 40. The delivery catheter includes an inner lumen through which the liquid medication is delivered. As can be seen in FIG. 3, the delivery catheter 40 includes a provided opening or slit 41 which opens upon a preselected fluid pressure being realized within the lumen of the delivery catheter. The delivery tip of the delivery catheter can be placed adjacent the site in the patient's body to which medication is to be delivered. Thus, the medication can be delivered directly to such a site for optimum effect.

Attached and connected in fluid flow communication with the inlet port 14 of the pump is a tubular conduit 52. The tubular conduit is attached also to the reservoir 42. Alternatively, an injection site assembly can be interconnected between the pump and reservoir along the tubular conduit as is shown in FIG. 3. The reservoir 42 includes a base member 50 to which is attached an expansible sheet or sidewall 54. The sidewall 54 is bonded to the base member 50 for providing a liquid-tight seal between the sidewall and base member. The sidewall 54 can expand or inflate to hold a sufficient volume of liquid medication from which an aliquot can be delivered to the patient through the pump. The sidewall 54 and base member 50 form a reservoir chamber 44 in the reservoir 42. The reservoir chamber 44 can be of any desired size depending upon the use of the overall assembly, expected time the assembly is to remain implanted in the patient, and volumes of the incremental doses of medication to be delivered over such time. Positioned within the reservoir chamber 44 is a collection tube 46. Such a collection tube can be a perforated tube having perforations 48 provided on its surface and opening into the lumen of the collection tube. Preferably, the collection tube 46 is positioned such that it lies within the chamber and is positioned along the perimeter of the reservoir chamber 44. In such an arrangement, the collection tube can collect substantially all of the liquid medication in the reservoir chamber 44 regardless of the orientation of the chamber and reservoir 42.

The tubular conduit 52 connects with the collection tube 46. The tubular conduit 52 can be interrupted and have provided along its length and injection site 56. The injection site can be any implantable injection site, such as disclosed in U.S. Pat. No. 4,190,040 of Schulte entitled "Resealable Puncture Housing For Surgical Implantation," the entire disclosure of which is incorporated herein by this reference.

The injection site includes a dome 58 which can be punctured with a needle cannula and, upon withdrawal of the needle cannula, reseals to prevent leakage. The use of an injection site along the tubular conduit 52 provides a method for refilling the reservoir 42 with additional liquid medication after the overall assembly has been implanted in a pateint. The injection site can be connected directly to the reservoir rather than in-line between the reservoir and pump.

To use the implantable demand medication delivery assembly herein, the entire assembly is implanted in a patient. As stated earlier, the entire assembly can be constructed of a biocompatible material, such as silicone elastomer. The delivery catheter 40 is implanted such that its tip is adjacent the stie to which the liquid medication is to be delivered. The delivery catheter can have any length. It is preferred to implant the pump in a readily accesible location so that it can be actuated by the patient. It is also desirable to provide the pump in a location where it will be somewhat inconspicuous and also will not be inadvertently bumped so as to cause an inadvertent delivery of medication. However, the design of the pump generally avoids such an inadvertent delivery.

After implantation, when the patient feels a need for delivery of medication or when a prescribed time period has elapsed so that a dosage of medication can be delivered, the patient depresses the dome portion 18 on the pump. The depression of the dome causes collapse of the dome in upon the reservoir chamber 22 in the pump, causing the liquid medication in the reservoir chamber 22 to flow through the second port 32, past the then open pressure regulated valve 36, and outwardly through the second fluid passage 34 and through the delivery conduit 40. The one-way valve 28 prevents the liquid medication in the reservoir chamber 22 from flowing through the first fluid passage 24. As the pressure on the dome portion 18 is relaxed, the dome portion 18 recovers to its original shape, causing a reduced pressure in the reservoir chamber 22. The reduced pressure draws additional liquid medication from the reservoir 42 through the tubular conduit 52 connecting the reservoir to the pump and through the one-way valve 28. Liquid medication is drawn into the reservoir chamber 22 of the pump until it has substantially filled the reservoir chamber with the desired aliquot of medication. The pressure regulated valve 36 also recovers closing the second port 32 to fluid flow, thereby retaining the new dosage of liquid medication in the reservoir chamber 22. Subsequently, as the patient requires an additional dosage of medication, the dome portion of the pump can again be depressed to deliver the liquid medication and the cycle is repeated.

In the event the liquid medication stored in the reservoir 42 becomes depleted and the patient continues to have a need for the assembly and delivery of medication, then a syringe filled with additional liquid medication can be used to replenish the liquid medication in the reservoir. The injection site 56 is palpated to determine its location. Once the injection site has been located, the injection site can be pierced with the needle cannula of the syringe. Additional liquid medication can then be injected into the injection site. The added liquid medication flows from the injection site into the reservoir 42. The liquid medication is prevented from flowing into and through the pump 10 due to the one-way valve present in the pump. The fluid pressure due to the presence of liquid medication in the reservoir chamber 22 of the pump maintains the one-way valve 28 closed, thereby occluding fluid flow through the first port out of the chamber. The fluid pressure in the first fluid flow passage and below the dome-shaped valve maintains the second port closed to fluid flow. the liquid medication introduced into the injection site, therefore, flows into the reservoir chamber 44 of the reservoir 42.

We claim:

1. An implantable demand medication delivery assemably comprising:
   a reservoir means for storing a liquid medication to be delivered;
   a pump means in fluid communication with the reservoir means for pumping a selected volume of the liquid medication, the pump means comprising:
      a base member having an inlet port in fluid communication with the reservoir means and an outlet port;
      a resilient deformable wall extending over the base member and defining a chamber between the resilient deformable wall and base member;
      a fluid passage having a first portion extending through the base member between the inlet port and the chamber and a second portion extending between the chamber and the outlet port;
      a one-way valve means in the first portion of the fluid passage between the inlet port and chamber for permitting fluid flow toward the chamber; and
      a pressure regulated valve means in the second portion of the fluid passage between the chamber and outlet port for selectively permitting fluid flow through such fluid passage at preselected fluid pressures; and
   a delivery catheter means connected to the outlet port of the pump means for delivering the liquid medication to a location spaced from the pump means.

2. An Assembly as recited in claim 1 wherein the resilient deformable wall of the pump means comprises a flexible resilient dome portion extending over the chamber and protective means for preventing inadvertent compression of the dome portion.

3. An assembly as recited in claim 2 wherein the protective means comprises a toroidal extension of the sidewall which projects beyond and encircles the flexible resilient dome portion.

4. An assembly as recited in claim 1 wherein the one-way valve means comprises a flap valve extending over a first port in the fluid passage and opening into the chamber whereby the presence of liquid in the chamber can exert a force on the flap valve and urge it against the first port to close the first port to fluid flow from the chamber.

5. An assembly as recited in claim 4 wherein the flap valve comprises a dome-shaped valve having an aperture therein and attached along its periphery to a wall of the chamber extending around the first port wherein the aperture and first port are misaligned such that a preselected fluid pressure in the chamber closes the flap valve to fluid flow.

6. An assembly as recited in claim 1 wherein the reservoir means comprises a resilient-walled, enclosed envelope defining a reservoir chamber therein and a length of perforated tubing in the chamber, which perforated tubing communicates with a tubular conduit extending between the reservoir means and inlet port of the pump means.

7. An assembly as recited in claim 6 wherein the length of perforated tubing extends along the periphery of the reservoir chamber.

8. An assembly as recited in claim 1 further comprising an implantable resealable injection site positioned in fluid communication with the reservoir means.

9. An assembly as recited in claim 8 wherein the injection site is provided between the reservoir means and the pump means along a tubular fluid passage conduit in fluid communication with the reservoir means and pump means.

10. An implantable demand medication delivery assembly comprising:
    a reservoir means for storing a liquid medication to be delivered;
    a pump means in fluid communication with the reservoir means for pumping a preselected volume of the liquid medication, the pump means comprising:
       a base member defining a first fluid passage extending from an inlet port to a first port opening on an upper surface of the base member and a second fluid passage extending between a second port opening in the upper surface of the base member to an outlet port;
       a resilient wall attached to the base member including an encircling dome portion extending over the first and second port openings of the base member to define a chamber between the resilient wall and base member; and
       a pressure regulated valve means in the second fluid passage for opening to permit fluid flow through the second fluid passage at preselected fluid pressures in the chamber upon actuation of the pump means; and
    a delivery catheter means connected to the outlet port of the pump means for delivering the liquid medication to a location spaced from the pump means.

11. An assembly as recited in claim 10 wherein the resilient wall of the pump means further comprises a barrier portion for inhibiting the inadvertent compression of the dome portion.

12. An assembly as recited in claim 11 wherein such barrier portion of the resilient wall comprises a toroidal extension of the resilient wall extending beyond and encircling the dome portion.

13. An assembly as recited in claim 10 further comprising a oneway valve positioned along the first fluid passage.

14. An assembly as recited in claim 13 wherein the one-way valve comprises a flap valve extending over the first port.

15. An assembly as recited in claim 14 wherein the flap valve comprises a dome-shaped valve attached along its periphery to a wall of the chamber having an aperture therein, which valve extends over the first port and the aperture and first port are misaligned such that a preselected fluid pressure in the chamber closes the valve to fluid flow from the chamber.

16. An assembly as recited in claim 10 wherein the pressure regulated valve means comprises a dome valve in a valve chamber along the second fluid passage.

17. An assembly as recited in claim 10 wherein the reservoir means comprises a resilient-walled, enclosed envelope defining a reservoir chamber therein and a length of perforated tubing in the chamber, which perforated tubing communicates with a tubular conduit extending between the reservoir means and inlet port of the pump means.

18. An assembly as recited in claim 17 wherein the length of perforated tubing extends along the periphery of the reservoir chamber.

19. An assembly as recited in claim 10 further comprising an implantable resealable injection site positioned in fluid communication with the reservoir means.

20. An assembly as recited in claim 19 wherein the injection site is provided between the reservoir means and the pump means along a tubular fluid passage conduit in fluid communication with the reservoir means and pump means.

21. An assembly as recited in claim 16 wherein the dome valve references three pressures such that increased pressure in the first fluid passage tends to urge closed the valve thus preventing flow through the device.

* * * * *